United States Patent
Bonner, Jr. et al.

(10) Patent No.: US 7,691,831 B2
(45) Date of Patent: *Apr. 6, 2010

(54) PHARMACEUTICAL COMBINATION AND METHOD FOR TREATMENT OF REACTIVE ARTHRITIS OR BURSITIS

(75) Inventors: Ernest L. Bonner, Jr., 1406 Park St., Suite 400, Alameda, CA (US) 94501; Robert Hines, 3637 Cape Center Dr., Fayetteville, NC (US) 28304

(73) Assignees: Ernest L. Bonner, Jr., Alameda, CA (US); Robert Hines, Fayetteville, NC (US)

( * ) Notice: Subject to any disclaimer, the term of this patent is extended or adjusted under 35 U.S.C. 154(b) by 1300 days.

This patent is subject to a terminal disclaimer.

(21) Appl. No.: 11/096,260

(22) Filed: Mar. 29, 2005

(65) Prior Publication Data

US 2005/0272673 A1    Dec. 8, 2005

Related U.S. Application Data

(63) Continuation-in-part of application No. 11/054,921, filed on Feb. 9, 2005, which is a continuation-in-part of application No. 10/896,612, filed on Jul. 20, 2004, now Pat. No. 7,053,073, which is a continuation-in-part of application No. 10/271,117, filed on Oct. 15, 2002, now Pat. No. 6,765,000, which is a continuation-in-part of application No. 09/510,704, filed on Feb. 22, 2000, now Pat. No. 6,465,473, which is a continuation-in-part of application No. 09/270,962, filed on Mar. 17, 1999, now Pat. No. 6,087,382.

(51) Int. Cl.
*A61K 31/65* (2006.01)
*A61K 31/519* (2006.01)

(52) U.S. Cl. .................... 514/152; 514/154; 514/262.1; 514/398

(58) Field of Classification Search ................. 514/152, 514/154, 262.1, 398
See application file for complete search history.

(56) References Cited

U.S. PATENT DOCUMENTS

| | | | |
|---|---|---|---|
| 2,946,801 A | 7/1960 | Fields | |
| 3,148,212 A | 9/1964 | Boothe et al. | |
| 3,226,436 A | 12/1965 | Petisi et al. | |
| 4,159,338 A * | 6/1979 | Cherkofsky et al. | 514/397 |
| 4,177,796 A | 12/1979 | Franco-Vila | |
| 4,521,411 A | 6/1985 | Koloff | |
| 4,992,365 A * | 2/1991 | Hyman | 435/34 |
| 5,262,173 A | 11/1993 | Sheth et al. | |
| 5,523,297 A | 6/1996 | Pruzanski et al. | |
| 5,559,114 A * | 9/1996 | Exley | 514/81 |
| 5,728,680 A | 3/1998 | Morozov et al. | |
| 5,952,367 A | 9/1999 | Pak | |
| 5,972,389 A | 10/1999 | Shell et al. | |
| 6,034,122 A | 3/2000 | Chayen | |
| 6,087,382 A | 7/2000 | Bonner, Jr. et al. | |
| 6,093,414 A | 7/2000 | Capelli | |
| 6,197,776 B1 | 3/2001 | Bonner, Jr. et al. | |
| 6,326,364 B1 | 12/2001 | Lin et al. | |
| 6,416,779 B1 | 7/2002 | D'Augustine et al. | |
| 6,465,473 B1 | 10/2002 | Bonner, Jr. et al. | |
| 6,765,000 B2 | 7/2004 | Bonner, Jr. et al. | |
| 7,053,073 B2 | 5/2006 | Bonner, Jr. et al. | |
| 2002/0031558 A1 | 3/2002 | Yoo | |
| 2002/0151519 A1 | 10/2002 | Shepard | |
| 2003/0055022 A1 | 3/2003 | Bonner, Jr. et al. | |
| 2005/0059640 A1 | 3/2005 | Bonner, Jr. et al. | |
| 2005/0137181 A1 | 6/2005 | Bonner, Jr. et al. | |
| 2005/0176690 A1 | 8/2005 | Bonner, Jr. et al. | |
| 2006/0172956 A1 | 8/2006 | Bonner et al. | |

OTHER PUBLICATIONS

Astrauskiene, D., "Efficacy of empirically prescribed amoxicillin and amoxicillin+ clavulanic acid in children's reactive arthritis: a randomized trial," Clin Exp Rheumatol. Jul.-Aug. 2003;21(4):515-21.

Ayoub et al., "Poststreptococcal Reactive Arthritis," Curr Opin Rheumatol. Jul. 2000;12(4):306-10.

Bardin, T., "Antimicrobial Therapy in Inflammatory Joint Disease," Rev Rhum Engl Ed. Nov. 1998;65(11):625-9.

Bardin et al., "Antibiotic Trials in Reactive Arthritis," Rev Rhum Engl Ed. Jan. 30, 1999;66(1 Suppl):63S-66S.

(Continued)

*Primary Examiner*—Raymond J Henley, III
(74) *Attorney, Agent, or Firm*—Brian Beverly; Beeson Skinner Beverly

(57) ABSTRACT

A method for treatment for conditions in human beings associated with either or both reactive arthritis or bursitis comprising administering a combination of a member from each of the following groups of medications: (1) synthetic purine nucleoside analog antiviral drugs, (2) antibiotic drugs, and (3) imidazole drugs. Alternate embodiments of the invention include dual combinations of (A) a member of the synthetic purine nucleoside analog group of antiviral drugs and a member of the antibiotic group of drugs, (B) a member of the antibiotic group of drugs and a member of the imidazole family of drugs, and (C) a member of the synthetic purine nucleoside analog group of antiviral drugs and a member of the imidazole group of drugs.

9 Claims, No Drawings

OTHER PUBLICATIONS

Bell et al., "Management of sexually acquired reactive arthritis in 19 North Thames GUM clinics," Int J STD AIDS, Mar. 2004;15(3):195-8.

Birdi et al., "Acute rheumatic feaver and poststreptococcal reactive arthritis: diagnostic and treatment practices of pediatric subspecialists in Canada,": J Rheumatol. Jul. 2001;28(7):1681-8.

Brandt et al., "Effects of doxycycline on progression of osteoarthritis: results of a randomized, placebo-controlled, double-blind trial," Arthritis Rheum. Jul. 2005;52(7):2015-25.

Burnette et al., "Purification and Characterization of a Rat Liver Enzyme that Hydrolyzes Valaciclovir, the $_L$-Valyl Ester Prodrug of Acyclovir," Chem. Abs. AN#1995;673023, J. Biol. Chem., 270(26), 15827-31.

Ceroni et al., "Risks and complications of prolonged parenteral antibiotic treatment in children with acute osteoarticular infections," Acta Orthop Belg. Oct. 2003;69(5):400-4.

Fryden et al., "Early antibiotic treatment of reactive arthritis associated with enteric infections: clinical and serological study," BMJ, Dec. 8, 1990;301(6764):1299-302.

Hopkinson, N., "Sexually-acquired reactive arthritis," Hosp Med. Feb. 2001;62(2):83-5.

Kamphuisen et al., "Two years of penicillin prophylaxis is sufficient to prevent clinically evident carditis in poststreptococcal reactive arthritis," J Intern Med. Nov. 2001;250(5):449-52.

Kloppenburg et al., "Antimicrobial therapy for rheumatoid arthritis," Baillieres Clin Rheumatol. Nov. 1995;9(4):759-69.

Kocak et al., "Poststretptococcal Reactive Arthritis: Clinical Course and Outcome in 15 Patients," Turk J Pediatri. Apr.-Jun. 2000;42(2):101-4.

Kvien et al., "Three month treatment of reactive arthritis with azithromycin: a EULAR double blind, placebo controlled study," Ann Rheum Dis. Sep. 2005;63(9):1113-9.

Laasila et al., "Antibiotic treatment and long term prognosis of reactive arthritis," Ann Rheum Dis. Jul. 2003;62(7):655-8.

Lehman et al., "Clinical trials for post-streptococcal reactive arthritis," Curr Rheumamtol Rep. Oct. 2001;3(5):363-4.

Leirisalo-Repo, M., "Therapeutic aspects of spondyhloarthropathies—a review," Scand J Rheumatol. 1998;27(5):323-8.

Loffler et al, "*Clostridium difficile*-associated reactive arthritis in two children," Joint Bone Spine. Jan. 2004;71(1):60-2.

Morfin Maciel et al., "Reactive polyarthritis and painful dermatographism caused by *Helicobacter pylori*," Rev Alerg Mex. May-Jun. 2002;49(3):99-102. Article in Spanish; abstract only is provided in English.

Neumayr et al., "Chronic reactive arthritis associated with Calmette-Guerin bacillus," Dtsch Med Wochenschr. Sep. 13, 2002;127(37):1886-8. Article in German; abstract only is provided in English.

Palazzi et al., "Reactive arthritis: advances in diagnosis and treatment," Reumatismo. Apr.-Jun. 2002;54(2):105-12. Article in Italian; abstract only is provided in English.

Palazzi et al., "Management of reactive arthritis,"Expert Opin Pharmacother. Jan. 2004;5(1):61-70.

Pappas et al., "Unusual causes of reactive arthritis: Leptospira and *Coxiella bumetii*," Clin Rheumatol. Oct. 2003;22(4-5):343-6.

Pott et al. letter, "Long-term antibiotic treatment in reactive arthritis," Lancet. Jan. 30, 1988;1(8579):245-6.

Shulman et al., "Poststreptococcal reactive arthritis," Curr Opin Rheumatol. Sep. 2002;14(5):562-5.

Sieper et al., "Report on the Fourth International Workshop on Reactive Arthritis," Apr. 2000; Arhritis Rheum.;43(4):720-34.

Sieper, J., "Reactive arthritis: practical procedure in diagnosis and problematic aspects of antibiotic therapy," Z Rheumatol. Apr. 2003;62(2):110-1. Article in German; abstract only is provided in English.

Sieper et al., "No benefit of long-term ciprofloxacin treatment in patients with reactive arthritis and undifferentiated oligoarthritis: a three-month, multicenter, double-blind, randomized, placebo-controlled study," Arthritis Rheum. Jul. 1999;42(7):11386-96.

Sieper et al., "Expert Witness Reports in Rheumatology," British Society for Rheumatology, 1998;37:715-20.

Smieja et al., "Randomised, blinded, placebo controlled trial of doxycycline for chronic seronegative arthritis," Ann Rheum Dis. Dec. 2001; 60(12):1088-94.

Svenungsson, B., "Reactive arthritis," Int J STD AIDS. May-Jun. 1995;6(3):156-60.

Toivanen et al., "Reactive Arthritis," Curr Opin Rheumatol. Jul. 1997;9(4):321-7.

Toivanen et al., "Effect of antimicrobial treatment on chronic reactive arthritis," Clin Exp Rheumatol. May-Jun. 1993;11(3):301-7.

Toivanen et al., "Reactive arthritis," Best Practice & Research Clinical Rheumatology, Oct. 2004;18(5):689-703.

Toivanen, A., "Bacteria-Triggered reactive arthritis: implications for antibacterial treatment," Drugs. 2001;61(3):343-51.

Zhang et al., "Experimental Yersinia-triggered reactive arthritis: effect of a 3-week course of ciprofloxacin," Br J Rheumatol. May 1997;36(5):541-6.

Lichtman et al., "Reactivation of Arthritis Induced by Small Bowel Bacterial Overgrowth in Rats: Role of Cytokines, Bacteria, and Bacterial Polymers", *Infection and Immunity*, 63(6):2295-2301 (1995).

Schirmer et al., "Acyclovir in Acute Oligoarticular Herpetic Arthritis", *Lancet*, 346(8976):712-713 (1995).

Stebbings et al., "Chickenpox Monoarthritis: Demonstration of Varicella-Zoster Virus in Joint Fluid by Polymerase Chain Reaction", *British Journal of Rheumatology*, 37:311-313 (1998).

Toussirot et al., "Do Minocycline and Other Tetracyclines Have a Place in Rheumatology", *Rev. Rheum Engl. Ed.*, 64(7-9):474-480 (1997).

Acyclovir package Insert from South African Electronic Package Inserts, 3 pages, published Oct. 1, 1997.

Arnold et al., "Poststreptococcal reactive arthritis", *Annals of the Rheumatic Diseases*, 48(8):686-688 (1989).

NDA 05-733 for Zithromax Injection, 218 pages (Azithromycin) dated Jan. 30, 1997.

Swanson, J.M. and Chenitz, W.C., "The prevention and management of genital herpes: a community health approach", *Journal of Community Health Nursing*, 6(4):209-221 (1989).

Tuffrey et al., "The effect of a single oral dose of azithromycin on chlamydial infertility and oviduct ultrastructure in mice", *Journal of Antimicrobial Chemotherapy*, 34:989-999 (abstract only) (1994).

* cited by examiner

PHARMACEUTICAL COMBINATION AND METHOD FOR TREATMENT OF REACTIVE ARTHRITIS OR BURSITIS

CROSS-REFERENCES TO RELATED APPLICATIONS

This application is a continuation-in-part of U.S. patent application Ser. No. 11/054,921 filed on Feb. 9, 2005, which is a continuation-in-part of U.S. patent application Ser. No. 10/896,612 filed on Jul. 20, 2004, now U.S. Pat. No. 7,053,073, which is a continuation-in-part of U.S. patent application Ser. No. 10/271,117 filed on Oct. 15, 2002, now U.S. Pat. No. 6,765,000, which is a continuation-in-part of U.S. patent application Ser. No. 09/510,704, filed on Feb. 22, 2000, now U.S. Pat. No. 6,465,473, which is a continuation-in-part of U.S. patent application Ser. No. 09/270,962 filed on Mar. 17, 1999, now U.S. Pat. No. 6,087,382.

BACKGROUND OF THE INVENTION

This invention relates to an improved method for treatment of symptoms associated in humans with reactive arthritis or idiopathic bursitis.

Reactive arthritis refers to a spondyloarthritity which usually arises as a complication of an infection elsewhere in the body. Reactive arthritis can be caused by species of *Shigella* bacteria (most notably *Shigella flexneri*), *Yersinia enterocolitica*, *Campylobacter jejuni*, several species of *Salmonella*, genitourinary pathogens, *Chlamydia trachomatis*, *Neisseria gonorrhea*, *Ureaplasma urealyticum*, *Streptococcus pyogenes*, and other yet unidentified infectious agents.

Reactive arthritis commonly occurs in young men and women, but can occur at any age. Sufferers experience joint pain, stiffness, redness or swelling. Common symptoms may include fatigue, malaise, fever, and weight loss. The joints of the lower extremities, including the knee, ankle, and joints of the foot, are the most common sites of involvement, but symptoms can also occur in the wrists, fingers, elbows, shoulders, neck, and lower back. Other symptoms may include urethritis and prostatitis in males, and cervicitis or salpingitis in females. Ocular disease is common ranging from transient, asymptomatic conjunctivitis to aggressive anterior uveitis that occasionally results in blindness. Mucocutaneous lesions and nail changes are frequent. On less frequent or rare occasions manifestations of reactive arthritis include cardiac conduction defects, aortic insufficiency, central or peripheral nervous system lesions, and pleuropulmonary infiltrates.

Treatment of patients suffering from reactive arthritis with nonsteroidal anti-inflammatory drugs ("NSAIDs") provides some benefit, although symptoms of reactive arthritis are rarely completely alleviated and some patients fail to respond at all. The preferred initial treatment of choice for acute reactive arthritis is indomethacin in divided doses of 75 to 150 milligrams per day. The NSAID of last resort is phenylbutazone, in doses of 100 milligrams twice or three times per day, because of its potentially serious side effects. Patients with debilitating symptoms refractory to NSAID therapy may be treated with cytotoxic agents such as azathioprine or methotrexate, or with sulfasalazine. Tendinitis, other lesions, and uveitis may benefit from corticosteroids. Minocycline hydrochloride, a semisynthetic derivative of tetracycline, is indicated for infections caused by at least *Shigella* microorganisms, *Streptococcus pyogenes*, and *Neisserie gonorrhoeae*. It is therefore an accepted treatment in incidents of reactive arthritis triggered by these biological entities.

Long-term follow-up studies have suggested that some joint symptoms persist in many, if not most, patients with reactive arthritis. Recurrences of the more acute symptoms are common and as many as twenty-five percent of patients either become unable to work or are forced to change occupations because of persistent joint problems.

Bursitis is inflammation of a bursa, a thin-walled sac lined with synovial tissue. The function of the bursa is to facilitate movement of tendons and muscles over bony prominences. Bursitis may be caused by excessive frictional forces, trauma, systemic disease such as rheumatoid arthritis or gout, or infection. The most common form of bursitis is subacromial. Trochanteric bursitis causes patients to experience pain over the lateral aspect of the hip and upper thigh, and tenderness over the posterior aspect of the greater trochanter. Retrocalcaneal bursitis involves the bursa located between the calcaneus and the posterior surface of the Achilles tendon. Pain is experienced at the back of the heel, and swelling appears on either or both of the medial and lateral sides of the tendon. Retrocalcaneal bursitis occurs in association with spondyloarthritities, rheumatoid arthritis, gout, and trauma.

Treatment of bursitis generally consists of prevention of the aggravating condition, rest of the involved part, an NSAID, and local steroid injection. In the long term, bursitis can result in loss of use of a joint and chronic pain syndrome.

The long term effects of reactive arthritis and bursitis range from chronic pain to crippling disability. It is also thought that many instances of osteoarthritis and psoriatic arthritis are in actuality reactive arthritis. Unfortunately, current procedures for management treat the symptoms of these diseases rather than their underlying pathogens.

It is known that the combination of minocycline hydrochloride, InH, and metronidazole inhibits the multiplication of susceptible organisms, including *shigella, salmonella, chlamydia, streptococci*, and *mycobacteria*. Yet, no effective pharmaceutical combination exists which is effective to put the diseases of reactive arthritis and bursitis into remission or to effect a cure.

SUMMARY OF THE INVENTION

Significant benefits can be obtained by treating humans affected with conditions associated with reactive arthritis or bursitis using combinations of acyclovir, minocycline hydrochloride, and metronidazole or, alternatively, valacyclovir hydrochloride, minocycline hydrochloride, and metronidazole.

Acyclovir and valacyclovir hydrochloride are members of the family of synthetic purine nucleoside analog antiviral drugs.

Minocycline hydrochloride is a member of the tetracycline family. It has been shown to be effective against gram-negative bacteria, some gram-positive bacteria and other microorganisms.

Metronidazole is a member of the nitroimidazole family. Metronidazole is an oral synthetic antiprotozoal and antibacterial agent.

One embodiment of a combination for treatment of the symptoms in human beings of reactive arthritis or idiopathic bursitis, or both, comprises the combination of acyclovir, minocycline hydrochloride, and metronidazole. An alternative combination comprises the substitution of valacyclovir hydrochloride in place of acyclovir. The pharmaceutical dosages of the compounds of the combination may be administered in capsules, tablets, in suspension form, or by injection.

The invention discloses a pharmaceutical combination, and a method for administration of a pharmaceutical combination, that puts the diseases of reactive arthritis and bursitis into remission. Treatment with the combination may effect a cure of reactive arthritis and bursitis, but definitive testing has not been performed to confirm that fact.

DETAILED DESCRIPTION OF THE INVENTION

Applicants have determined that a method of treatment involving administration of a combination of L-lysine, minocycline hydrochloride, and metronidazole provides a medically effective treatment for reactive arthritis and bursitis. See U.S. Pat. No. 6,087,382. An alternate method includes administration of InH for those individuals who have tested positively for mycobacterial exposure, along with the underlying combination of L-lysine, minocycline hydrochloride, and metronidazole. Id. It has also been shown that the combination of acyclovir, L-lysine, minocycline hydrochloride, and metronidazole provides an effective treatment for these conditions. See U.S. Pat. No. 6,197,776. Individuals with severe symptoms, including joint swelling and joint contractures, who were not thought to be candidates for treatment using the combination of L-lysine, minocycline hydrochloride, and metronidazole only, have also experienced substantial beneficial effects in response to treatment with that combination and valacyclovir hydrochloride. See U.S. Pat. No. 6,465,473 to Bonner, Jr., et al. A third method of treatment, described in applicants' U.S. Pat. No. 6,197,776, includes administration of acyclovir with the underlying combination of L-lysine, minocycline hydrochloride, and metronidazole. A further embodiment of the treatment, described in applicants' U.S. Pat. No. 6,765,000, comprises a pharmaceutical combination for a single capsule formulation including acyclovir, minocycline hydrochloride, and metronidazole. Alternatively, the treatment may include valacyclovir hydrochloride, minocycline hydrochloride, and metronidazole. Any of the above embodiments may be supplemented with administration of pyridoxine hydrochloride, glucosamine, manganese, vitamin C, and desalinated seawater, such as Essence of Life.

Applicants have now determined that a medically effective treatment for reactive arthritis and bursitis involves administration of a combination of medicines drawn from the following three groups of medications: (1) synthetic purine nucleoside analog antiviral drugs ("Antivirals"), (2) broad spectrum antibiotic drugs including members of the tetracycline, quinolone, beta-lactam, macrolide, and ketolide families ("Antibiotics"), and (3) members of the imidazole group of drugs including members of the nitroimidazole and benzimidazole families ("Imidazoles"). With each group, particular medicines which are medically effective, in combinations according to the invention, will be discussed in greater detail below.

Acyclovir and valacyclovir hydrochloride are members of the Antivirals group. The chemical name of acyclovir is 2-amino-1,9-dihydro-9-[(2-hydroxyethoxy)methyl]-6H-purin-6-one. Acyclovir is commercially available under the brand name ZOVIRAX® in capsules, tablets, or suspension. Acyclovir has demonstrated anti-viral activity against herpes simplex virus types I and II, varicella-zoster virus, Epstein-Barr virus and cytomegalovirus, both in vitro and in vivo. Like L-lysine, acyclovir inhibits herpes simplex viruses, but by a different mechanism. While L-lysine tends to stop the virus from replicating by inhibiting the initiation of the replication process, acyclovir inhibits effective replication of actively replicating viral particles, e.g., by stopping replication of herpes viral DNA. This is accomplished by either competitive inhibition or inactivation of viral DNA polymerase or incorporation and termination of the growing viral DNA chain. It is believed that acyclovir results in a substantial benefit due to its inhibition of virus replication. In double-blind testing, it has been found that the administration of the combination of acyclovir, minocycline hydrochloride, and metronidazole is an effective treatment for reactive arthritis or bursitis. Acyclovir has never been used in the prior art for treatment of arthritis or bursitis. It does not appear to be effective alone for the treatment of these diseases. The preferred dose of acyclovir is 400 mg twice daily. The daily dose of acyclovir may vary from 200 mg to 4 grams.

Valacyclovir hydrochloride (sold under the brand name Valtrex®) is the hydrochloride salt of L-valyl ester of acyclovir. The chemical name of valacyclovir hydrochloride is L-valine 2-[(2-amino-1,6-dihydro-6-oxo-9H-purin-9-yl)methoxy]ethyl ester, monohydrochloride. Valacyclovir hydrochloride is rapidly and nearly completely converted to acyclovir in the body. The preferred dose of valacyclovir hydrochloride is 500 mg twice daily. The total daily dose of valacyclovir hydrochloride may vary from 125 mg to 4 grams.

Other members of the Antivirals which are medically effective substitutes for acyclovir and valacyclovir hydrochloride, in the combination according to the invention, are penciclovir, famciclovir, ganciclovir and valganciclovir and their metabolites.

The preferred drug for practicing the invention falling within the Antibiotics group is minocycline hydrochloride. Minocycline hydrochloride is a member of the tetracycline family of Antibiotics. Minocycline hydrochloride is a bacteriostatic antibiotic which exerts its antimicrobial effect by inhibition of bacterial protein synthesis. It has been shown to be effective against gram-negative bacteria, some gram-positive bacteria and other microorganisms. The preferred dose of minocycline hydrochloride is an initial dosage of 200 mg followed by doses of 100 mg twice per day. Daily doses of minocycline hydrochloride following the initial administration of 200 mg may vary from 50 mg to 200 mg. Other members of the tetracycline family which are medically effective substitutes for minocycline hydrochloride as an Antibiotic in the combination according to the invention include: chlortetracycline, oxytetracycline, demeclocycline, methacycline, doxycycline, and tigecycline and their metabolites.

Other Antibiotic drugs which, in the combination described above, are medically effective substitutes for minocycline hydrochloride are members of the quinolone, beta-lactam, macrolide, and ketolide families. Members of the Quinolone family of Antibiotics which are medically effective substitutes for minocycline hydrochloride include: nalidixic acid, cinoxacin, norfloxacin, ciprofloxacin, oflaxacin, sparfloxacin, lomefloxacin, leroxacin, pefloxacin, levofloxacin, trovafloxacin, clinafloxacin, gatifloxacin, moxifloxacin, and sitafloxacin and their metabolites.

Members of the beta-lactam family of Antibiotics which are medically effective substitutes for minocycline hydrochloride include: penicillin V, penicillin G, methicillin, nafcillin, oxacillin, dicloxacillin, ampicillin, amoxicillin, carbenicillin, ticarcillin, mezlocillin, piperacillin, cefuoxime axetil, cefpodoxime proxetil, cephalexin, cebadroxil, loracarbef, cefaclor, cephalothin, cefazolin, cefamandole, cefoxitin, cefuroxime, cefonicid, cefotetan, ceforanide, cefotaxime, ceftriaxone, ceftizoxime, cefoperzone, ceftazidime, cefepime and their metabolites. Beta-lactams are widely considered to be a medically acceptable alternative to tetracyclines. Amoxicillin is a semi-synthetic antibacterial agent with a broad spectrum of bactericidal activity. The preferred dose of amoxicillin is 500 mg twice per day. The total dose per day of amoxicillin may vary from 50 mg to 3 gm.

Members of the macrolide family of Antibiotics which are medically effective substitutes for minocycline hydrochloride include: erythromycin, clarithromycin, and axithromycin and their metabolites. Azithromycin acts by interfering with microbial protein synthesis and has a wide spectrum of activity against microorganisms. Members of the macrolide family are widely considered to be a medically acceptable alternative to tetracyclines. The preferred dose of azithromycin is 125 mg twice per day. The total dose per day of azithromycin may vary from 50 mg to 2 gm.

Telithromycin is a member of the ketolide family of antimicrobial agents. Telithromycin is a semi-synthetic antibacterial agent which acts by blocking protein synthesis. Members of the ketolide family are widely considered to be a medically acceptable alternative to tetracyclines. The preferred dose of telithromycin is 400 mg twice per day. The total dose per day of telithromycin may vary from 50 mg to 2 gm.

The preferred drug for practicing the invention falling within the Imidazole group is metronidazole, a member of the nitroimidazole family of Imidazoles. The preferred dose of metronidazole is 250-500 mg twice per day. The total dose per day of metronidazole may vary from 100 mg to 1,000 mg. Other members of the nitroimidazole family which are medically effective substitutes for metronidazole in a combination according to the invention include: tinidazole, ornidazole, secnidazole and benznidazole and the metabolites thereof. Members of the benzimidazole family which are medically effective substitutes for metronidazole include nitazoxanide, thiabendazole, and albendazole and the metabolites thereof.

The preferred embodiment of the present invention comprises the combination of acyclovir, or its prodrug valacyclovir hydrochloride, with minocycline hydrochloride and metronidazole in a single capsule formulation. Alternate embodiments of the invention comprise substitutions for one or more of the drugs of the preferred embodiment with medically acceptable substitutes selected from the groups and families of drugs discussed above. Additionally, alternate embodiments of the invention include dual combinations in a single capsule formulation of (A) Antivirals and Antibiotics, (B) Antibiotics and Imidazoles, and (C) Antivirals and Imidazoles. Dual combinations of Antivirals and Antibiotics include: (1) a member of the Antivirals group and a member of the macrolide family of Antibiotics, (2) a member of the Antivirals group and a member of the beta-lactam family of Antibiotics, (3) a member of the Antivirals group and a member of the ketolide family of Antibiotics, (4) a member of the Antivirals group and a member of the tetracycline family of Antibiotics and (5) a member of the Antivirals group and a member of the quinolone family of Antibiotics. Dual combinations of Antibiotics and Imidazoles include: (1) a member of the ketolide family of Antibiotics and a member of the Nitroimidazole family, (2) a member of the beta-lactam family of Antibiotics and a member of the Nitroimidazole family of Imidazoles, and (3) a member of the macrolide family of Antibiotics and a member of the Nitroimidazole family of Imidazoles, (4) a member of the Nitroimidazole family of Imidazoles and a member of the tetracycline family of Antibiotics, and (5) a member of the Nitroimidazole family of Imidazoles and a member of the quinolone family of Antibiotics, (6) a member of the ketolide family of Antibiotics and a member of the Benzimidazole family, (7) a member of the beta-lactam family of Antibiotics and a member of the Benzimidazole family of Imidazoles, and (8) a member of the macrolide family of Antibiotics and a member of the Benzimidazole family of Imidazoles, (9) a member of the Benzimidazole family of Imidazoles and a member of the tetracycline family of Antibiotics, and (10) a member of the Benzimidazole family of Imidazoles and a member of the quinolone family of Antibiotics. Dual combinations of Antivirals and Imidazoles include: (1) a member of the Antivirals group and a member of the nitroimidazole family and (2) a member of the Antivirals group and a member of the benzimidazole family.

These combinations each provide a medically effective treatment for reactive arthritis and bursitis. The total combination of medicines in each of these embodiments presents a broad spectrum approach that it is believed effectively addresses the underlying pathogenesis for reactive arthritis and what has previously been referred to as idiopathic bursitis, and further is a beneficial treatment for reactive arthritis in particular cases wherein the symptom complex has been misdiagnosed as osteoarthritis or psoriatic arthritis, or in any other similar cases of misdiagnosis.

Administration will generally be accomplished orally via single formulation capsules or tablets, in single formulation suspension form, or in independent dosages of single drug items in combination, but delivery could be accomplished by injection, or any other method commonly used for administration of internal medicines.

EXAMPLES

The following examples serve to illustrate the invention, but is not meant to restrict its effective scope.

Example 1

A 77 year old female presented with complaints of neck, upper back, lower back, bilateral shoulder, bilateral wrist, digits of hands, bilateral hip, and bilateral ankle pains of years duration. The patient complained of associated stiffness in those same joints. Her physical examination was remarkable for tenderness at her neck, right shoulder, elbow bilaterally, wrist bilaterally, the metacarpal phalangeal and the proximal interphalangeal joints of her right hand, hip bilaterally, knee bilaterally, and the Achilles insertion area bilaterally. The Sed rate and rheumatoid factors were normal. This patient was diagnosed with reactive arthritis and was started on a treatment consisting of single capsules—each capsule containing 125 mg of metronidazole, 250 mg of valacyclovir hydrochloride, and 50 mg of minocycline hydrochloride—twice daily. After 69 days of such treatment, the patient noted pain in the palm of her left hand only. She further denied any stiffness. Physical examination on the 69th day did not reveal any tenderness. Thus, treatment effected resolution of pain, stiffness, and tenderness in this patient.

Example 2

A 52 year old male presented with complaints of bilateral knee and left wrist pain. He also noted associated morning stiffness. He was treated with minocyline hydrochloride 100 mg BID and acyclovir 400 mg BID. This resulted in significant improvement, but not total resolution of his complaints of pain and stiffness in his knees and left wrist.

Example 3

A 45 year old male with multiple joint pain and associated stiffness who was treated with metronidazole 250 BID and minocycline 100 mg BID experienced a decrease in pain severity and a slight decrease in stiffness with such treatment.

There have been thus described certain preferred embodiments of a pharmaceutical formulation for treatment of conditions in human beings associated with either or both reactive arthritis or idiopathic bursitis. While preferred embodiments have been described and disclosed, it will be recognized by those with skill in the art that modifications are within the true scope and spirit of the invention. The appended claims are intended to cover all such modifications.

We claim:

1. A method for medically treating the symptoms of reactive arthritis or bursitis in humans comprising:
   administering to a patient an effective amount of the combination of a member of the group of synthetic purine nucleoside analog antiviral drugs or a pharmaceutically acceptable ester or a metabolite thereof, a member of the beta-lactam family or a metabolite thereof, and a member of the imidazole group or a metabolite thereof.

2. A method for medically treating the symptoms of reactive arthritis or bursitis in humans comprising:
   administering to a patient an effective amount of the combination of a member of the group of synthetic purine nucleoside analog antiviral drugs or a pharmaceutically acceptable ester or a metabolite thereof, a member of the macrolide antimicrobial family or a metabolite thereof, and a member of the nitroimidazole family or a metabolite thereof.

3. A method for medically treating the symptoms of reactive arthritis or bursitis in humans comprising:
   administering to a patient an effective amount of the combination of a member of the group of synthetic purine nucleoside analog antiviral drugs or a pharmaceutically acceptable ester or a metabolite thereof, and a member of the macrolide antimicrobial family or a metabolite thereof.

4. A method for medically treating the symptoms of reactive arthritis or bursitis in humans comprising:
   administering to a patient an effective amount of the combination of a member of the group of synthetic purine nucleoside analog antiviral drugs or a pharmaceutically acceptable ester or a metabolite thereof, and a member of the beta-lactam family or a metabolite thereof.

5. A method for medically treating the symptoms of reactive arthritis or bursitis in humans comprising:
   administering to a patient an effective amount of the combination of a member of the group of synthetic purine nucleoside analog antiviral drugs or a pharmaceutically acceptable ester or a metabolite thereof, a member of the ketolide antimicrobial family or a metabolite thereof, and a member of the imidazole group or a metabolite thereof.

6. A method for medically treating the symptoms of reactive arthritis or bursitis in humans comprising:
   administering to a patient an effective amount of the combination of a member of the group of synthetic purine nucleoside analog antiviral drugs or a pharmaceutically acceptable ester or a metabolite thereof, and a member of the ketolide antimicrobial family or a metabolite thereof.

7. A method for medically treating the symptoms of reactive arthritis or bursitis in humans comprising:
   administering to a patient an effective amount of the combination of a member of the imidazole group or a metabolite thereof and a member of the ketolide antimicrobial family or a metabolite thereof.

8. A method for medically treating the symptoms of reactive arthritis or bursitis in humans comprising:
   administering to a patient an effective amount of the combination of a member of the imidazole group or a metabolite thereof and a member of the beta-lactam family or a metabolite thereof.

9. A method for medically treating the symptoms of reactive arthritis or bursitis in humans comprising:
   administering to a patient an effective amount of the combination of a member of the imidazole group or a metabolite thereof and a member of the beta-lactam family or a metabolite thereof.

* * * * *